(12) United States Patent
Cook

(10) Patent No.: US 6,213,930 B1
(45) Date of Patent: Apr. 10, 2001

(54) METHOD OF USING ANTI-PHOSPHOLIPASE A2 ANTIBODIES TO ENHANCE GROWTH OR IMPROVE FEED EFFICIENCY

(75) Inventor: Mark E Cook, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/268,546

(22) Filed: Mar. 15, 1999

(51) Int. Cl.⁷ ........................................ A61K 31/19
(52) U.S. Cl. ........................................ 517/557
(58) Field of Search .......................... 514/557

(56) References Cited

U.S. PATENT DOCUMENTS

| | | | | |
|---|---|---|---|---|
| 5,080,895 | * | 1/1992 | Tokoro | 424/85.8 |
| 5,725,873 | * | 3/1998 | Cook et al. | 424/442 |
| 5,759,537 | * | 6/1998 | Garnett | 424/93.43 |
| 5,767,249 | | 6/1998 | Scheuer et al. | 530/388.26 |
| 5,821,264 | | 10/1998 | Lane et al. | 514/458 |
| 5,993,221 | * | 11/1999 | Bistrian | 424/429 |

FOREIGN PATENT DOCUMENTS

| | | |
|---|---|---|
| 41 42 552 A1 | 6/1993 | (DE). |
| PCT/DE88/00724 | 5/1990 | (WO). |
| PCT/US98/12340 | 12/1998 | (WO). |

OTHER PUBLICATIONS

Van Dullemen, et al. "Mediators of Mucosal Inflammation: Implications for Therapy," *Mucosal Inflammation* XP–000915056 92–98 (1997).

Feterel, et al., "Formation of Antibodies to Prostaglandins in the Yolk of Chicken Eggs," Abstract XP–002141604 (1982).

Baile, et al., "Hormones and Feed Intake," *Proc. Nutr. Soc.* 42:113–127 (1983).

Blikslager, et al., "Prostaglandins $I_2$ and $E_2$ Have a Synergistic Role in Rescuing Epithelial Barrier Function in Porcine Ileum," *J. Clin. Invest.* 100:1928–1933 (1997).

Duke, Gary E., "Recent Studies on regulation of Gastric Motility in Turkeys," *World's Poultry Science Association Invited Lecture*, pp. 1–8 (1991).

Hsueh, et al., "Injurious and Protective Mechanisms in the Gut," *Eicosanoids and Other Bioactive Lipids in Cancer Inflammation and radiation Injury* 3, 365–369 (1997).

McLaughlin, et al., "Effect of CCK Antibodies on Food Intake and Weight Gain in Zucker Rats," *Physiology & Behavior*, 34:277–282 (1983).

Reuter, et al, "Exacerbation of Inflammation–associated Colonic Injury in Rat through Inhibition of Cyclooxygenase–2," *J. Clin. Invest.*, 98:2076–2085 (1996).

Savory, et al., "Influence of Vagotomy in Domestic Fowls on Feeding Activity, Food Passage, Digestibility and Satiety Effects of Two Peptides," *Physiology & Behavior* 33:937–944 (1984).

Savory, et al., "Are there Hunger and Satiety Factors in the Blood of Domestic Fowls?," *Appetite*, 8:111–123 (1987).

Uribe, et al., "Endogenous Prostaglandins and Microflora Modulate DNA Synthesis and Neuroendocrine Peptides in the Rat Gastrointestinal Tract," *DNA Synthesis and Neuroendocrine Peptides*, 691–699 (1996).

\* cited by examiner

*Primary Examiner*—Kevin E. Weddington
(74) *Attorney, Agent, or Firm*—Quarles & Brady LLP

(57) ABSTRACT

A method for enhancing bodily growth or improving feed efficiency in animals reduces the availability of a prostaglandin or leukotriene precursor.

13 Claims, No Drawings

METHOD OF USING ANTI-PHOSPHOLIPASE A2 ANTIBODIES TO ENHANCE GROWTH OR IMPROVE FEED EFFICIENCY

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to a method for modulating the activity of one or more enzymes that produce precursors of lipid metabolites associated with gastric inflammation, to reduce the deleterious effects of gastric inflammation and to enhance animal and human growth or improve feeding efficiency.

Enhancing animal growth or feed efficiency, can have substantial impact on, for example, the animal meat industry by reducing the high cost of feeding food-producing animals and directly improving profitability. For example, in the poultry industry, even a slight increase in broiler growth rate coupled with reduced feed consumption brings the broiler to market maturity faster at lower cost. With approximately seven billion broilers raised annually in the United States, significant savings are realized.

Methods are known for controlling feeding behavior by modulating the activity of gut peptides that control gastrointestinal motility. These gut peptides include cholecystokinin (CCK), the avian pancreatic polypeptide (aPP), bombesin, gastrin, somatostatin, and neuropeptide Y. Duke, G. E., "Recent Studies on Regulation of Gastric Motility in Turkeys," *World's Poultry Science Association Invited Lecture*, pp. 1–8 (1991); Baile et al., "Hormones and feed intake," *Proc. Nutr. Soc.*, 42:113–27 (1983). The effect upon feeding behavior of physiological regulators other than the gut peptides is largely unknown.

One set of such regulators include inflammatory metabolites such as the leukotrienes and the prostaglandins which can have beneficial, as well as damaging, effects on the host.

In animals, linoleic acid is converted to arachidonic acid. Arachidonic acid is released (as arachidonate) from the sin 2 position of membrane phospholipids by phospholipase $A_2$ ($PLA_2$) and is converted by lipoxygenase or cyclooxygenase into precursors for biologically active prostaglandins and leukotrienes. Perhaps as a result of artificially high dietary linoleic acid levels, animals can contain high levels of the prostaglandin and leukotriene precursors.

Prostaglandins are $C_{20}$ fatty acids formed from arachidonic acid by cyclooxygenase activity. Prostaglandins cause inflammatory effects during gastrointestinal traumas, such as colitis and ulcers, and are involved in vasodilation, vasoconstriction, and stimulation of intestinal or bronchial smooth muscle. Prostaglandins are found in inflammatory exudates and can induce fever and erythema. Leukotrienes, which are formed from arachidonic acid in response to immunological or non-immunological leucocytes and macrophages stimulation, cause contraction of smooth muscle, such as intestinal smooth muscle, attract leukocytes and stimulate vascular permeability.

It may be possible to reduce inflammation by reducing gastrointestinal prostaglandin synthesis, perhaps by using selective inhibitors of cyclooxygenase-2, an enzyme expressed at inflammation sites. This would reduce or eliminate the need for standard nonsteroidal anti-inflammatory drugs which are known to have ulcerogenic side effects. However, Reuter et al. have shown that inhibition of cyclooxygenase products, such as prostaglandin, exacerbated colitis and increased inflammation-associated colonic injury. Reuter et al., "Exacerbation of Inflammation-associated Colonic Injury in Rat through Inhibition of Cyclooxygenase-2," *J. Clin. Invest.*, 98(9):2976–85 (1996). Likewise, Uribe et al. have shown that using indomethacin to inhibit prostaglandin synthesis causes intestinal ulcers. Uribe et al., "Endogenous Prostaglandins and Microflora Modulate DNA Synthesis and Neuroendocrine Peptides in the Rat Gastrointestinal Tract," *Scand. J. Gastro.*, 32:691–99 (1997). Other research has shown that prostaglandins are necessary for gut function repair. Blikslager et al., "Prostaglandins $I_2$ and $E_2$ Have a Synergistic Role in Rescuing Epithelial Barrier Function in Porcine Ileum," *J. Clin. Invest.*, 100(8): 1928–33 (1997).

These findings suggest that downregulating prostaglandin activity would be deleterious to an animal's gastrointestinal system.

BRIEF SUMMARY OF THE INVENTION

The present invention is summarized in that gastrointestinal inflammation is reduced, resulting in improved gut health, enhanced growth and increased feed efficiency in animals, without deleterious effect, by limiting bioavailability of a leukotriene and prostaglandin precursor.

In a related aspect, the invention is summarized in that the antibody can limit availability of arachidonic acid.

In another aspect of the invention, anti-$PLA_2$ antibodies are administered to an animal to increase growth or improve feed efficiency. The anti-$PLA_2$ antibodies limit availability of arachidonic acid, a precursor to inflammatory lipid metabolites such as leukotrienes and prostaglandins.

In yet another aspect of the invention, anti-PLA2 antibodies are administered to an animal to counteract inflammatory problems involving the gut, whether arising from exposure to endotoxin or infectious agents, or from inflammatory processes such as Crohn's.

It is an object of this invention to provide a method for reducing gastrointestinal tract inflammation, resulting in improved health, enhanced growth or increased feed efficiency in animals, without deleterious effect, by limiting availability of precursors to prostaglandin and leukotriene metabolites.

It is another object of the present invention to reduce availability of arachidonic acid without detrimental effect on the animal.

BRIEF DESCRIPTION OF THE SEVERAL VIEWS OF THE DRAWINGS

Not applicable.

DETAILED DESCRIPTION OF THE INVENTION

Prostaglandins and leukotrienes are believed to cause gastrointestinal inflammation which increases tissue damage and negatively affects the ability of animals, particularly mammals and avians, to convert feed into body weight. Limiting the availability of the precursors for these lipid metabolites reduces gut wall thickening, alters animal feeding behavior and improves animal health.

When the gut encounters endotoxins, Phospholipase $A_2$ ($PLA_2$) becomes active and an inflammatory response begins which can cause gut wall thickening and decreased weight gain. By limiting the production of lipid metabolites such as prostaglandin and leukotriene during normal food digestion, stimulation of intestinal smooth muscle is reduced, and more efficient feed conversion and bodily growth results. By limiting these lipid metabolites during gastrointestinal traumas, such as colitis and necrosis, inflammation is reduced and further tissue damage is avoided. The invention is preferably practiced on avian or mammalian animals. Preferred avian animals include chickens, ducks, turkeys, quail, and geese. Preferred mammalian animals include bovine, ovine, porcine, caprine, rodent and human animals.

In a preferred embodiment of the present invention, prostaglandin and leukotriene production is limited by decreasing the availability of arachidonate, a necessary precursor, by reducing or preventing arachidonate from being cleared from membrane phospholipids. One method for doing so involves interfering with phospholipase $A_2$ ($PLA_2$), the enzyme that clears arachidonate from membrane phospholipids. By reducing or preventing arachidonate release, the pool of available prostaglandin and leukotriene precursors is necessarily reduced.

The applicant has determined that by reducing the available arachidonate, the levels of prostaglandins and leukotrienes are reduced. The strategy is preferably practiced by preventing arachidonate release. This can be preferably achieved by reducing or eliminating activity of the $PLA_2$ enzyme. The $PLA_2$ enzyme activity can be reduced using an anti-$PLA_2$ antibody which, without intending to limit the applicant, is believed to complex with the $PLA_2$ enzyme and thereby interfere with its phospholipase activity. Polyclonal or monoclonal anti-$PLA_2$ antibodies can be prepared or administered using any of various methods known in the art to produce an antibody or antibody-like factor, including, but not limited to, production in transgenic plants or milk producing animals. Suitable antibodies can be, but need not be purified from non-antibody material present during preparation. Antibodies are considered suitable in the present method if they are able to reduce $PLA_2$ enzyme activity relative to untreated controls in side-by-side in vivo trials.

A skilled artisan can use other methods for reducing $PLA_2$ enzyme activity, such as a method of administering a non-antibody pharmaceutical agent that affects $PLA_2$ activity, in combination with a suitable carrier. One skilled in the art will also appreciate that the method can be practiced by introducing activity-altering changes to the genetic material of animals that encodes the $PLA_2$ enzyme or by interfering with transcription or translation of $PLA_2$. The agent can also limit the availability of a different precursor of prostaglandins or leukotrienes.

The agent can be administered by injection or by oral delivery, and is preferably administered in combination with a suitable carrier of the type commonly used in delivery of pharmaceuticals or nutritional supplements. Injection methods include, but are not limited to, subcutaneous, intraperitoneal, intramuscular, or intravenous injection. Oral administration, which is preferred, can include, but is not limited to, administration in tablet or powder form. Most preferably, the agent is fed directly by mixing with feed or by coating feed particles as described in U.S. Pat. No. 5,725,873, incorporated herein by reference in its entirety.

In a preferred method, antibodies are prepared as follows. A producer animal is immunized with a peptide or protein, such as $PLA_2$, against which antibodies are desired so that the producer animal produces an antibody to said peptide or protein. A substance containing the antibody is obtained from said producer animal. The antibody can be subject to further purification if desired or can be used without further preparation in an animal feed.

The method of Tokoro (U.S. Pat. No. 5,080,895), incorporated herein by reference in its entirety, can be used to produce a preparation of egg-yolk antibodies. Laying hens can be inoculated with $PLA_2$. Preferably, a suitable adjuvant is administered in conjunction with the hen $PLA_2$ inoculation to enhance the immunization. An adjuvant useful for this purpose is a water-in-oil emulsion adjuvant such as complete Freund's adjuvant. The $PLA_2$ causes the hens to produce anti-$PLA_2$ antibodies which are passively transferred into the egg yolk of eggs laid by the hens.

An egg preparation, e.g., egg yolks or whole eggs, containing the anti-$PLA_2$ antibody can be collected and homogenized to form an emulsion. The resulting emulsion can be dried to form a powder containing the anti-$PLA_2$ antibody. This powder can then be formulated in a manner appropriate to the administration route and then administered to the desired animals using methods known in the art. The preparation is preferably administered orally, most preferably as a supplement to the animal's diet.

The following examples are given to further illustrate the present invention. The present invention is not limited to the specific details set forth in the examples.

EXAMPLE

Chickens (laying hens) were injected intramuscularly with varying amounts of phospholipase $A_2$ ($PLA_2$) (0.05 to 10 mg) in complete Freund's adjuvant. Three weeks after the first injection, egg yolks or whole eggs containing antibody to $PLA_2$ were collected, and fed for 21 days at 0.0–0.5 g dietary dried egg yolk per kg feed to baby chicks (beginning at one day of age). Chicks were also fed egg yolks containing comparable amounts of anti-urease antibody.

Body weight and feed efficiency were determined fourteen and twenty-one days after feeding. See Table 1. On day fourteen, chicks fed anti-$PLA_2$ antibodies, on average, exhibited a two point improvement in feed conversion efficiency (1.58 vs. 1.60) and gained 41 grams of body weight more than untreated control chicks. Feed conversion efficiency is defined as the amount of feed in grams required to cause an animal to gain 1 gram of weight. A 100 point improvement in feed efficiency corresponds to a decrease of 1 gram in the amount of feed required to cause the animal to gain 1 gram. In view of the substantial market for, e.g., broiler chickens in the U.S. alone (7 billion per year), a point of improvement has significant commercial effect in reduced feed cost. On day twenty-one, chicks fed anti-$PLA_2$ antibodies, on average, exhibited a four point improvement in feed conversion efficiency (1.68 vs. 1.72) and gained 57 grams of body weight more than untreated control chicks.

TABLE 1

Effects of $PLA_2$ Treatment on Young Chickens

| Treatment | Feed Conversion average ± SEM (range) | Weight Gain average ± SEM (range) |
| --- | --- | --- |
| Week 2 | | |
| Control | 1.60 ± 0.023 (1.53 – 1.67) | 304 ± 15 (262 – 316) |
| Anti-PLA2 | 1.58 ± 0.038 (1.50 – 1.68) | 345 ± 11 (324 – 366) |
| Anti-Urease | 1.75 ± 0.161 (1.55 – 2.07) | 315 ± 6 (300 – 328) |

TABLE 1-continued

Effects of PLA$_2$ Treatment on Young Chickens

| Treatment | Feed Conversion average ± SEM (range) | Weight Gain average ± SEM (range) |
|---|---|---|
| Week 3 | | |
| Control | 1.72 ± 0.02 | 599 ± 24 |
| Anti-PLA2 | 1.68 ± 0.06 | 656 ± 29 |
| Anti-Urease | 1.66 ± 0.01 | 615 ± 26 |

The present invention is not intended to be limited to the foregoing, but to encompass all such modifications and variations as come within the scope of the appended claims.

I claim:

1. A method for enhancing growth or feeding behavior of an animal relative to a control animal, the method comprising administering to said animal an agent that reduces the bioavailability in the animal of a prostaglandin or leukotriene lipid precursor, wherein the agent comprises an antibody.

2. The method as claimed in claim 1, wherein the prostaglandin or leukotriene lipid precursor is arachidonic acid.

3. The method as claimed in claim 1, wherein the agent prevents release of the lipid precursor from a phospholipid.

4. The method as claimed in claim 1, wherein the agent comprises an anti-phospholipase A$_2$ (anti-PLA$_2$) antibody.

5. The method as claimed in claim 1 wherein the agent is administered by a method selected from the group consisting of injection and oral delivery.

6. The method as claimed in claim 1 wherein the agent is administered by an injection method selected from subcutaneous injection, intraperitoneal injection, intramuscular injection, and intravenous injection.

7. The method as claimed in claim 1, wherein the agent is mixed with a feed or food.

8. The method as claimed in claim 1, wherein the animal is selected from the group consisting of an avian and a mammal.

9. The method as claimed in claim 8, wherein the avian is selected from the group consisting of a chicken, a turkey, or a duck.

10. The method as claimed in claim 8, wherein the mammal is selected from the group consisting of a bovine, an ovine, a porcine, a caprine, a rodent and a human.

11. A method as claimed in claim 1 wherein the step of administering the antibody comprises the step of feeding the animal an egg preparation that comprises the antibody.

12. An animal feed that comprises an anti-PLA$_2$ antibody.

13. An animal feed as claimed in claim 12 that comprises an egg preparation comprising an anti-PLA$_2$ antibody.

* * * * *